United States Patent [19]

Dickhudt

[11] Patent Number: 4,465,079

[45] Date of Patent: Aug. 14, 1984

[54] BIOMEDICAL LEAD WITH FIBROSIS-INDUCING ANCHORING STRAND

[75] Inventor: Eugene A. Dickhudt, St. Paul, Minn.

[73] Assignee: Medtronic, Inc., Minneapolis, Minn.

[21] Appl. No.: 434,032

[22] Filed: Oct. 13, 1982

[51] Int. Cl.³ .............................................. A61H 1/04
[52] U.S. Cl. ................................. 128/785; 128/419 P
[58] Field of Search ............................... 128/784–786, 128/419 P

[56] References Cited

U.S. PATENT DOCUMENTS 3,902,501 9/1975 Citron et al. .......................... 128/785
4,026,303 5/1977 Babotai ................................ 128/785
4,407,303 10/1983 Akerstrom ........................... 128/785

Primary Examiner—Lee S. Cohen
Attorney, Agent, or Firm—Reed A. Duthler; John L. Rooney; Joseph F. Breimayer

[57] ABSTRACT

A biomedical stimulation lead for implanting in a living body having non-woven strands of fibrotic-inducing material attached to the distal tip of the lead for anchoring the lead in the body. The strands are sufficiently pliant to pull out of the fibrotic material along the path defined by the position of the strand within the fibrotic material, whereby the lead may be removed from the body with relatively minor trauma to body tissues.

7 Claims, 6 Drawing Figures

U.S. Patent  Aug. 14, 1984  4,465,079
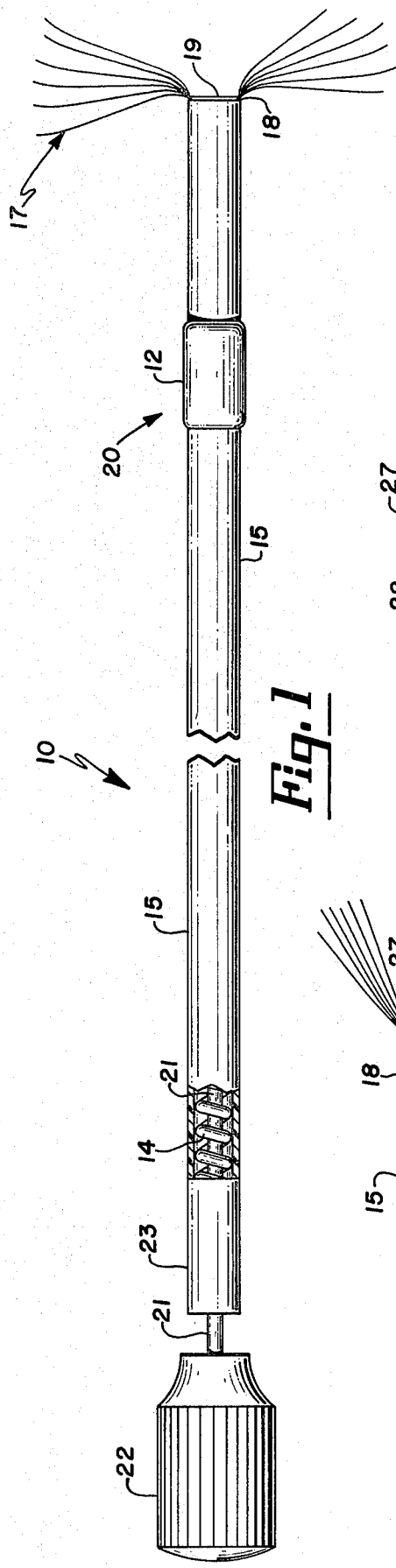
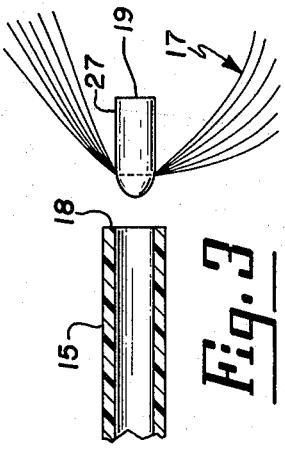
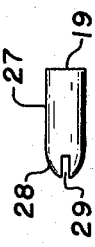
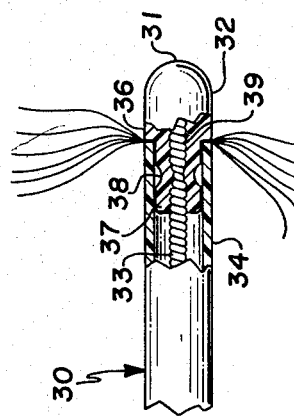
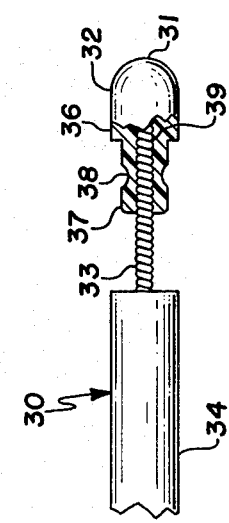
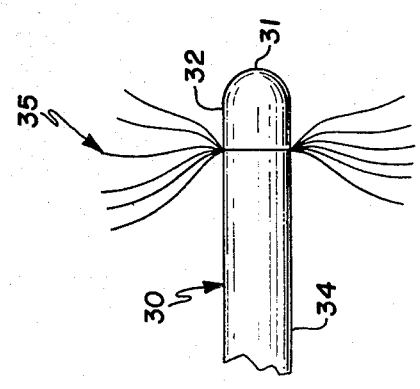

BIOMEDICAL LEAD WITH FIBROSIS-INDUCING ANCHORING STRAND

BACKGROUND OF THE INVENTION

1. Field of the Invention

This invention in general relates to the field of leads for the electrical stimulation of living tissue, and more particularly concerns a lead having improved means for anchoring the lead which, at the same time, permits the lead to be removed from the body with relatively minor trauma to body tissues.

2. Description of the Prior Art

Electrical stimulation of the body is an increasingly important medical procedure. For example, electrical stimulation of the heart with devices commonly known as heart pacemakers has become a routine method of treating heart block and other heart ailments, while electrical stimulation of the spinal cord has proven to be effective in relieving chronic pain. The present invention involves a lead which is particularly well-suited for use in the latter context. In this context, a lead is introduced into the epidural space which surrounds the spinal cord. One end of the lead, generally called the proximal end of the lead, is attached to a source of electrical pulses, while the other end of the lead which is within the epidural space and is generally called the distal end of the lead, includes an exposed electrode by which the electrical stimulation is applied to the spinal cord.

A problem encountered in many stimulation contexts, and in particular in the context of the stimulation of the spinal cord within the epidural space, is the dislodgment of the electrode after insertion. Many different means for anchoring the distal end of the lead, including the electrode, in or about the tissue to be stimulated, have been devised. One method that is well known for anchoring the distal end of the lead is the use in at least a portion of the distal tip of the electrode of materials which enhance fibrotic growth. These materials serve to anchor the lead by stimulating the growth of fibrotic tissue about the lead, causing the lead to become enmeshed in the fibrotic material thereby anchoring it. For example, U.S. Pat. No. 3,737,579 discloses a woven netting made of Dacron ®, a material which enhances fibrotic growth, which netting is affixed to the lead at a location just proximal to the electrode with the intention that fibrotic tissue will grow into the netting, thereby firmly affixing the electrode to the tissue to be stimulated, such as the heart muscle. Another known lead designed for use in the epidural space includes an area along the lead body which is roughened with a fibrotic growth-inducing material such as Dacron ®. The roughening consists of tiny stiff nubs of Dacron ® covering a cylindrical surface area about the outer casing of the lead.

In the case of such leads which employ fibrosis-inducing materials, the fibrotic material becomes closely interwoven with the lead-anchoring material as it grows. For example, the case of U.S. Pat. No. 3,737,579 the fibrotic growth becomes interwoven in the mesh of the netting, and in the second described type of lead, the fibrotic tissue wedges between the Dacron ® nubs. Should it become necessary to remove the leads after the fibrotic growth has occurred, neither of the prior art leads can be removed without tearing away from or through the fibrotic material. This tearing process can cause trauma to the normal body tissue to which the fibrosis is attached, and also can create problems caused by the residue of fibrotic material which is torn away. This torn-away material is of particular concern in the case of leads that are implanted in the epidural space, since trauma to the spinal cord can cause considerable pain and possible permanent damage.

SUMMARY OF THE INVENTION

It is an object of the invention to provide a biomedical stimulation lead which can be anchored using fibrosis-inducing structures without one or more of the disadvantages of the prior art disclosed above.

It is a further object of the invention to provide a biomedical stimulation lead which includes an anchoring means employing fibrotic-inducing materials which may be withdrawn from the fibrotic material with relative little or no damage to either the fibrotic material or the neighboring body tissue. It is another object of the invention to provide a stimulation lead which is particularly well-suited for stable placement within the epidural space. It is a further object of the invention to provide a stimulation lead which firmly resists movement of the electrode due to body motion and other normal causes of dislodgement, but which may be easily removed by pulling the lead from the body cavity in which it is implanted.

It is another object of the invention to provide a lead which satisfies the above object, and at the same time, can be inserted into the epidural space using conventional techniques.

The invention provides a biomedical stimulation lead for implantation in a living body comprising an exposed electrode, and an electrical conductor connected to said electrode and encased in a material which is generally inert to body fluids. The lead includes a strand means extending from the lead from a location near the distal end of the lead for holding the electrode in position, these strand means being formed of a material which enhances fibrotic growth and being sufficiently pliant to pull through the fibrotic material along the path defined by the position of the strand means within the fibrotic material when the lead is pulled from the body, so that the lead may be removed from the body with relatively minor trauma to body tissues. In one aspect of the invention, the strands comprise a plurality of Dacron ® fibers attached to the distal tip of the lead. In other aspects of the invention, the fibers may be attached to a location between the electrode and the distal tip of the lead or at a location proximal to the electrode.

It has been found that the lead as described above has surprising stability within the epidural space. It has developed that the property which permits it to be easily removed from the body cavity with the strands pulling through the fibrotic tissue, without tearing the tissue, also contributes to increase stability. That is, the relative flexibility of the strands as compared to the body tissues causes the strands to bend, curl, and form themselves into irregular shapes as the lead is introduced into the body cavity and the strands come in contact with tissue. A fibrosis then grows about the bent and curled and other irregular shapes of the strands which form surfaces which hold the lead securely against normal forces exerted on it such as body motion, etc. Numerous other features, objects, and advantages of the invention will become apparent from the following detailed description, when read in conjunction with the accompanying drawings.

BRIEF DESCRIPTION OF THE DRAWINGS

FIG. 1 is a partially cutaway side view of a lead according to the invention;

FIG. 2 is a top view of a plug according to the invention for securing the strands to the lead shown in FIG. 1;

FIG. 3 is a side view showing the plug of FIG. 2 with the strands in place across the notch of the plug, with the plug about to be inserted into the end of the lead of FIG. 1;

FIG. 4 is an alternative embodiment of the lead according to the invention;

FIG. 5 is a partially cutaway side view of the lead of FIG. 4 partially assembled, with the electrode portion being partially cutaway; and FIG. 6 is a partially cutaway side view of the electrode of FIG. 4 showing the strands in place between the electrode and the insulating sheath.

DESCRIPTION OF THE PREFERRED EMBODIMENT

A biomedical stimulation lead 10 according to the invention is shown in FIG. 1. Lead 10 includes an exposed electrode 12, connected to an electrical conductor 14, the conductor 14 being encased in an insulating sheath 15 which is generally inert to body fluid. The principal feature of the present invention comprises flexible strand means 17, which, in the embodiment shown in FIG. 1, are attached to the extreme distal end 18 of the lead 10. Strand means 17 serve to anchor the distal end 20 of the lead in the body in which the lead is implanted, as shall be described in more detail below. Also shown in FIG. 1 is a stylet comprised of stylet wire 21 and stylet knob 22, the stylet being insertable into the lead in order to stiffen the lead when it is being implanted, but which is removed from the lead after implantation.

FIG. 2 shows a top view of a plug 27 according to the invention for securing the strand 17 in the end 18 of the insulating sheath 15. Plug 27 is a bullet-shaped member having a flat end 19 and a rounded end 28, and having a diameter which is just slightly larger than the internal diameter of sheath 15 so that it fits securely in the sheath 15.

FIG. 3 shows a plug 27 with the strand 17 in place in notch 29 in position to be inserted into sheath 15. Plug 27 is pushed into sheath 15 until plug end 19 is flush with sheath end 18. Medical adhesive may be placed over the ends 18 and 19 after plug 27 is inserted in sheath 15 in order to further secure the plug in the sheath. Alternatively, adhesive may be placed about the diameter of plug 27 to secure the plug.

FIG. 4 shows the distal portion of an alternative embodiment of lead 30 according to the invention. This embodiment includes an exposed electrode 32 forming the extreme distal end of lead 30, and strands 37 which are attached to lead 30 at the point of juncture between electrode 32 and sheath 34.

FIG. 5 shows a partially assembled lead 30, detailing the connection between the electrode 32 and the conductor 33. Electrode 32 includes a head portion 36 having a rounded extreme distal tip 31 and a cylindrical rear portion 37. A cylindrical bore 39 extends from approximately midway in the head portion 36 to the end of rear portion 37. To assemble the lead, conductor 33 is inserted into bore 39, and then rear portion 37 is crimped at 38 to secure electrode 32 to conductor 33. Strands 37 are then placed against the end 37 of electrode 32 and sheath 34 is slipped over the strands 35 in the end 37 so that the strands 35 are grasped between the sheath 34 and the electrode 32, as shown in FIG. 6. Medical adhesive may also be used to assist in securing strands 35, sheath 34, and electrode 32 together in this embodiment also.

Strands, such as 17 and 35, are formed of a material which enhances the growth of fibrotic tissue in the body, such as polyester fiber. Preferably, they are made out of Dacron ® which is a trademark of E. I. DuPont DeNemours and Company for one type of polyester fiber. The preferred embodiment of the strands are approximately 0.0005–0.001 inches in diameter and 0.375 to 0.500 inches long. However, any size strands may be used provided the strands are sufficiently pliant that, when the lead is pulled from its implanted position in the body, the strands pull out of fibrotic material along the path defined by the position of the strands in the fibrotic material. The electrodes such as 32 and 12 are preferably made of platinum, but may be made of any suitable metal or other conductive material. The conductors, such as 14 and 33 are helical coiled conductors having a lumen 21 passing down the central axis of the coil, which conductors are well known in the prior art. Likewise, the stylet 21, 22 is well known in the prior art. Sheath 15 is made of any insulating material which is generally inert to body fluids, such as polyurethane or silicone rubber, as is also well known in the prior art.

When a lead according to the invention, such as 20 or 30, is implanted in the body, the strands such as 17 or 35 tend to assume irregular positions in the area about the distal end of the lead. Within a matter of hours, fibrotic material begins to grow about the strands such as 17 and 35, and within a matter of days, sufficient fibrotic material has grown so that the strands become anchored in the material. The fibrotic material will then continue growing about the strands until the strands such as 17 and 35 are completely embedded in the material, and form channels in the fibrotic material, the channels being defined by the position of the strand in the body, and the fibrotic material grows about it. It has been found that these strands, such as 17 and 35, provide excellent anchorage for the distal end of the lead against movement of the end of the lead and the electrode, such as 12 or 32 under normal body movement. It is a feature of the invention that, when it is desired to remove the lead from the body, and the lead is pulled out of the body tissue, the strands are sufficiently pliable that they follow the path of least resistance through the fibrotic material and pull cleanly out of the fibrotic material following the channel formed by the strands within the material. Thus, in contrast to the prior art leads, when the leads are removed from the body, the strands do not tear or rip apart the fibrotic material or pull the fibrotic material from the body tissue, with the additional danger of damaging the body tissue. Since the necessity of removing the electrodes is a relatively common occurrence, such a feature is highly desirable.

Another feature of the invention is the flexibility of the strands and ease of implantation of the lead in the body with conventional methods. Conventionally, such leads are implanted in the body through a Touhy needle, which requires the parts of the lead to be small to pass through the needle. It is a feature of the invention that the strands pass easily through the needle and then spread out broadly about the area of the distal end of the lead to secure a firm foothold for the lead.

Generally the length of the lead 20 between distal end 18 and electrode 12 is about 1 cm., so that the strands 17 do not cause fibrotic growth about electrode 12, which may interfere with the stimulation of the electrode. The electrode of the embodiment of FIG. 4 is generally used with fewer strands, or is used in conditions where the strands are swept backward from the electrode upon implantation, in order to minimize the amount of fibrosis about tip 31.

There is no set number of strands such as 17 and 35 that must be used. It has been found that good fixation was found with leads employing from 20 to 40 strands. A larger number of strands may be used when it is desired that the growth of fibrosis be rapid. A lesser number of strands may be used in cases where the patient will be immobile for a sufficient period of time after the lead is implanted to permit fibrosis growth to firmly embed the strand means.

There has been described a novel biomedical stimulation lead that provides for greatly improved electrode stability and can be inserted into the epidural space by conventional means, and at the same time, can be withdrawn from the body with minimal trauma to body tissues. While the invention has been described in connection with two particular embodiments, one skilled in the art will appreciate that numerous other embodiments and departures from the embodiments shown may be made without departing from the inventive concepts. For example, a wide variety of sizes of strands may be used, and a variety of strand materials may be used within the limitations described. In addition, other features may be added to the lead, while still employing the inventive elements. It is therefore to be understood that, within the scope of the appended claims, the invention may be practiced other than as it has been specially described.

I claim:

1. A biomedical stimulation lead for implantation in a living body, of the type having a lead body having a proximal end and a distal end, an exposed electrode, an electrical conductor connected to said electrode and a sheath of a material which is generally inert to body fluids, said lead further comprising:

fixation means extending from said lead body from a location near the distal end of said lead body for holding said electrode in position within said living body, said fixation means comprising a plurality of strands having a first end attached to said lead body and a second end extending from said lead body and formed of a material which enhances fibrotic growth, and being sufficiently pliant to pull out of fibrotic material along the paths defined by the positions of said strands in said fibrotic material, whereby said lead may be removed from said living body with relatively minor trauma to body tissues.

2. A lead as in claim 1 wherein said strands are formed of a polyester fiber.

3. A lead as in claim 1 wherein said strands are between 0.0005 and 0.001 inches in diameter and between 0.375 and 0.500 inches long.

4. A lead as in claim 1 wherein said fixation means is located at the distal end of said lead body.

5. A lead as in claim 1 wherein said strands are located proximally of said electrode.

6. A lead as in claim 1 wherein said strands are located distally of said electrode.

7. A lead as in claim 1 wherein said strands comprise from about 20 to 40 strands.

* * * * *